United States Patent [19]

Weiler et al.

[11] Patent Number: 5,072,721
[45] Date of Patent: Dec. 17, 1991

[54] PATIENT REST FOR LITHOTRIPTER

[75] Inventors: Herbert Weiler, Alling; Peter Buchbauer, Garching; Siegfried Hofsaess, Germering, all of Fed. Rep. of Germany

[73] Assignee: Dornier Medizintechnik, Munich, Fed. Rep. of Germany

[21] Appl. No.: 513,611

[22] Filed: Apr. 24, 1990

[30] Foreign Application Priority Data

May 11, 1989 [DE] Fed. Rep. of Germany ....... 3915381

[51] Int. Cl.⁵ ............................................. A61B 17/22
[52] U.S. Cl. ............................. 128/24 EL; 269/328; 378/209
[58] Field of Search ........ 128/24 EL, 24 AA, 660.02; 269/322, 324, 328; 378/208, 209

[56] References Cited

U.S. PATENT DOCUMENTS

| 3,428,307 | 2/1969 | Hunter et al. | 378/209 |
| 3,452,977 | 7/1969 | Ryman | 378/209 |
| 3,652,851 | 3/1972 | Zaalberg | 378/209 |
| 3,751,028 | 8/1973 | Scheininger et al. | 378/209 |
| 4,552,346 | 11/1985 | Schnelle et al. | 378/209 |
| 4,575,064 | 3/1986 | Menor | 378/209 |
| 4,870,954 | 10/1989 | Satoh | 128/24 AA |

FOREIGN PATENT DOCUMENTS

| 0221325 | 5/1987 | European Pat. Off. | 128/24 EL |
| 3532678 | 3/1987 | Fed. Rep. of Germany | 128/24 EL |
| 2413073 | 8/1979 | France | 378/209 |

OTHER PUBLICATIONS

Direx, Tripter X1, 7-12-89.
Siemens, "Lithostar", 7-12-89.
Dornier MFL 5000 Technical Description, 7-12-89.
Dornier MFL 5000 The Urological Unit, 7-12-89.

Primary Examiner—Lee S. Cohen
Assistant Examiner—Krista M. Pfaffle
Attorney, Agent, or Firm—R. H. Siegemund

[57] ABSTRACT

A lithotripter having a central housing for equipment pertaining to shockwave generation, further having a focusing equipment head movably connected thereto, is improved by an up and down sliding patient rest having a central horizontally positioned cantilever mounted segment with a closure as treatment window; a headrest is removably attached to one side of the central segment; and leg support structure such a rest segment with extension or a miction pan or leg support troughs is removably attached to the opposite side of the central segment.

5 Claims, 2 Drawing Sheets

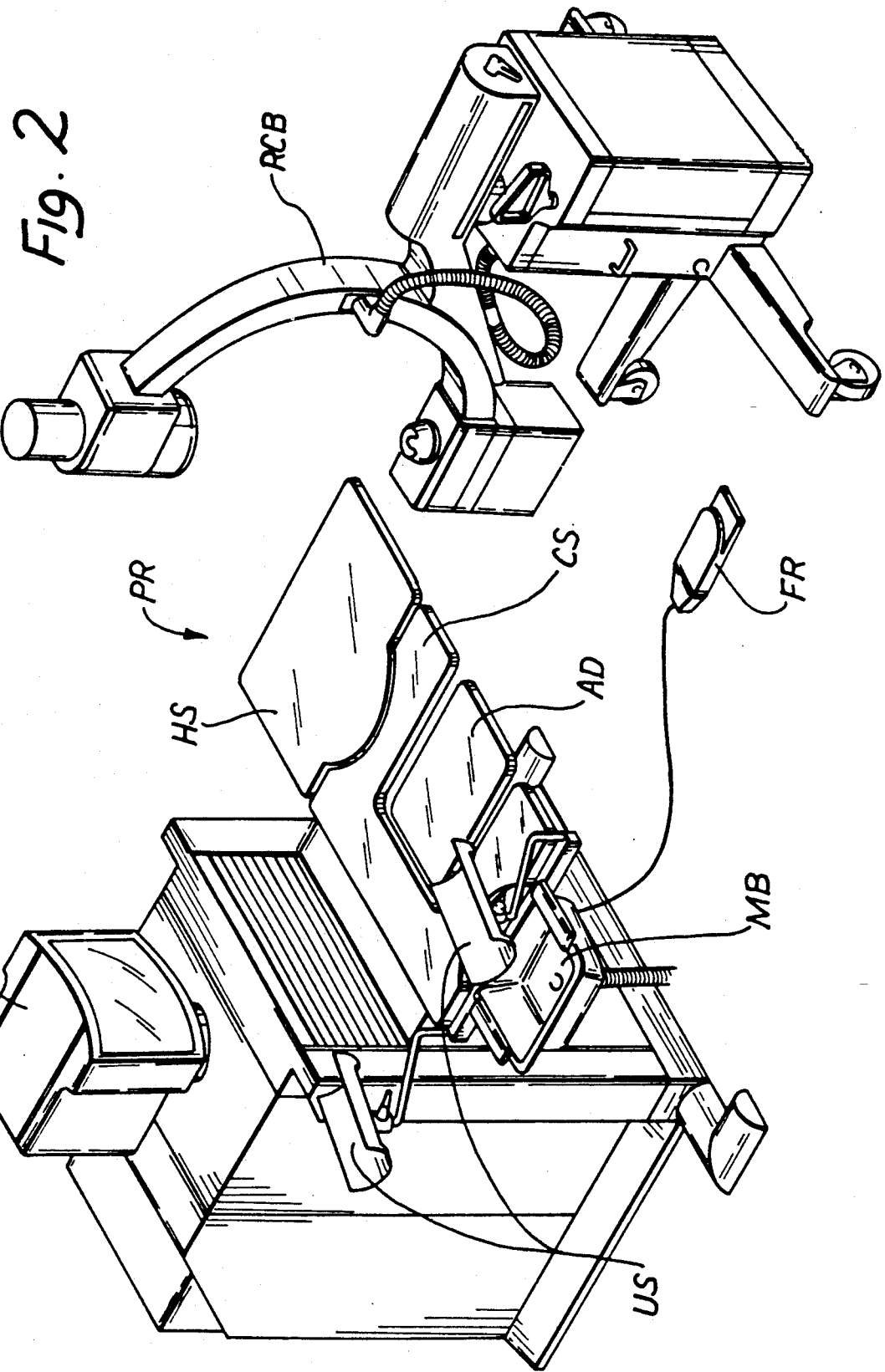

PATIENT REST FOR LITHOTRIPTER

BACKGROUND OF THE INVENTION

The present invention relates to a rest for patients, and more particularly to equipment for placing and holding a patient in a resting and reclining position, to be used for example in direct cooperation and association with a lithotripter.

German patent 3201021 describes a rest of the kind and variety to which the invention pertains, wherein particularly the rest surface area supporting the shoulders as well as the thighs can be inclined strongly in relation to each other. Further equipment of the general kind to which the invention pertains is shown in U.S. Pat. No. 4,705,026 or U.S. Pat. No. 4,669,483. Also the literature mentioned in these references is of relevant interest as to the background and state of the art generally.

DESCRIPTION OF THE INVENTION

It is an object of the present invention to provide a new and improved patient rest which is adaptable and usable in lithotripsy specifically but also for urology generally and other invasive procedures.

In accordance with the preferred embodiment of the present invention it is suggested to provide a rest and patient support such as to have a central segment or rest portion which is provided with a window and is constructed for plug-in of a head rest portion on one side of the central rest segment, and of a foot portion at the opposite sideof the central rest segment.

Thus it can be seen that the invention is comprised of a rest which is constructed from a plurality of plug-in parts for cooperation with a central segment or rest portion being a central element. That central element has a coverable "treatment" window in relation to which other rest portions can be plugged in which then become head and foot rest segments. The central segment is, in the case of lithotripsy, actually a laterally cantilever extension of the housing or casing of the equipment for the lithotripsy equipment and the head and foot segments are then attached in turn to the central part. Basically it does not make any difference what is the foot and what is the head portion. Standing in front of the lithotripter with the central segment extending towards the viewer one will be attached to the right and the other to the left.

In furtherance of the invention there may be a basic attachment which is to be used for the head supporting segment and will be a portion of the foot supporting segment, as the latter is further extendable through a foot extension segment. One can readily see that a great versatility is preceded here, in that one has, say, a single foot/head rest segment which by itself is used on both sides of the central segment and both of them are subject to extension through extending segment, so that one of them then becomes the foot proper but this depends in what position one wishes the patient to have vis-a-vis the lithotripter. This is important in the case where a distinction is necessary which is usually based on the question of whether the right or the left kidney is treated or whether or not the patient is placed on the stomach or on the back.

The window in the central segment should be "closable" through an insert so that the entire rest offers a more or less continuous surface with only certain small gaps where abutting parts join. The modularity of the rest is also made clear on the basis of providing lower leg or a miction pan instead of the foot segment. This will be necessary in case the rest is used for urological or surgical procedures in still another variety the head and foot segments are just similar relatively long pieces.

DESCRIPTION OF THE DRAWINGS

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

FIG. 2 is basically a similar view with similar equipment shown in FIG. 1 but supplemented by urological or other equipment.

Proceeding now to the detailed description of the drawings, FIG. 1 illustrates a lithotripter generally which includes a bare equipment housing GE. Housing GE has a front wall ET from which extends basically a patient rest PR. That rest is comprised of a central segment CS and extensions as will be described. The lithotripter includes a therapeutic head TK by means of which shockwaves will be focused e.g. into a concrement in a kidney or the like inside of a patient or the rest. The lithotripter includes in addition a monitor M with a display window W showing e.g. an X-ray or ultrasonic sound image of the area that is subject to treatment.

Figure 1:
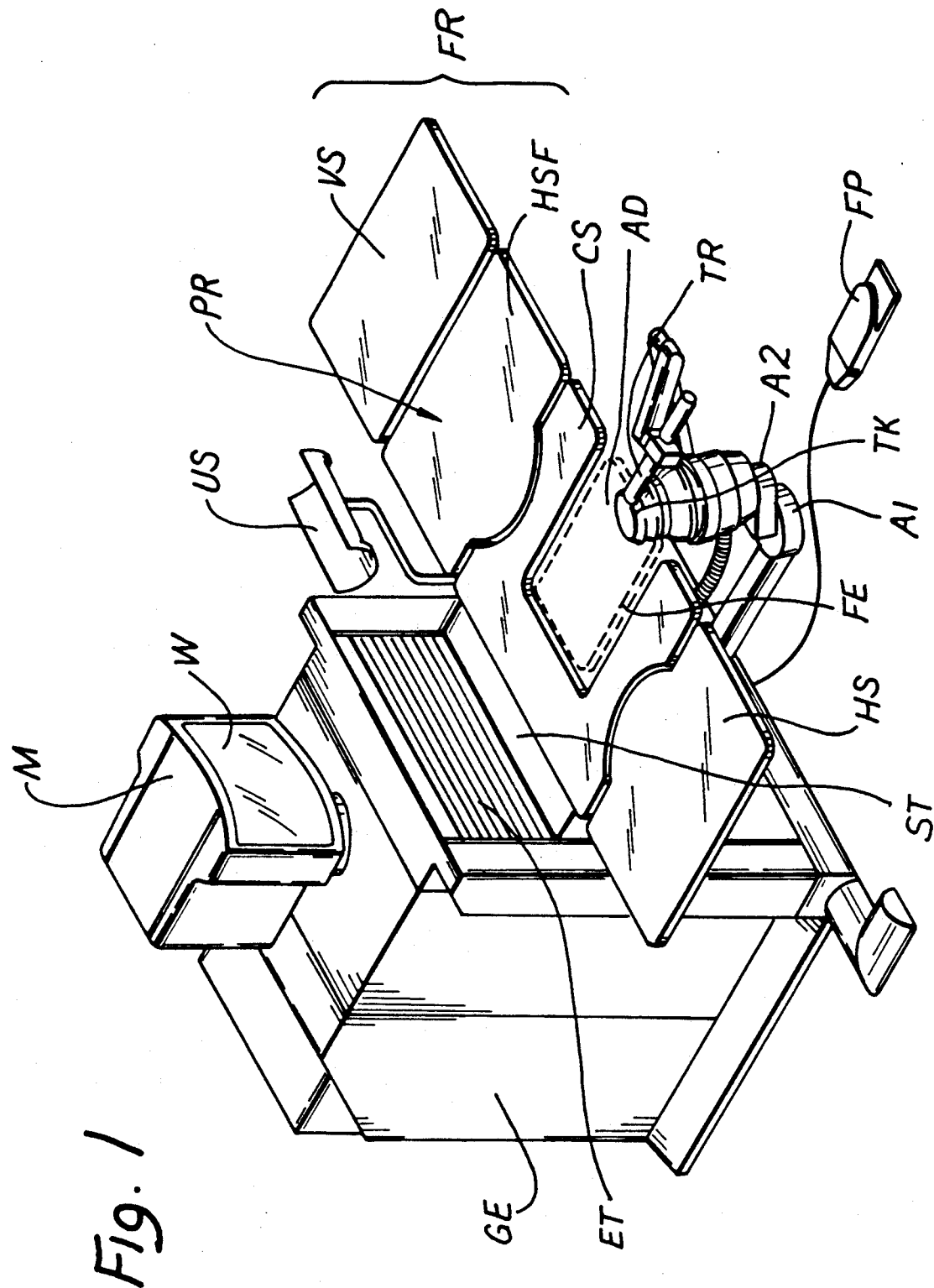
FIG. 1 is a perspective view of equipment that includes a patient rest in accordance with the preferred embodiment of the present invention for practicing the best mode thereof.

The central panel for the patient rest CS is mounted to a floating table portion ST and can be horizontally shifted in relation thereto. The table ST is affixed to the front wall ET by means of which the rest can be shifted up or down. Therefore the housing GE includes a suitable drive operated e.g. by a foot pedal FP, the front wall ET of the equipment is of an up and down sliding variety.

The central rest portion ZS is provided with a window FE which is shown however to be reduced in its dimensions or closed by a cover AD. An extension segment HS is fastened to the right side of the central panel or segment CS and another extension, identified by HSF, is affixed to the left hand side. This extension segment can best be described as a head/foot segment. The left panel or segment HS is the head rest proper and the right hand panel is provided with an extension VS, and together this right hand side segment HSF and the extension VS serve as the foot rest FR. In addition or alternatively lower leg support pieces such as US can be attached to the central panel.

The therapeutic head TK is fastened to the housing GE through arms A1 and A2 and is in fact positioned or positionable next to or under the window FE. The therapeutic head TK carries in addition ultrasonic transducer TR which is the imaging and locating equipment of the lithotripter. The respective image is of course visible in the window W of monitor M. The head and foot segment and various portions can be changed or positioned so that the foot rest is to the left and the head rest is the right of the equipment.

FIG. 2 illustrates a modified arrangement, the arrangement is not modified in principle but in terms of detailing the equipment. For the sake of variety the HS segment which has served as head rest in FIG. 1 is now affixed to the right hand side of the central segment CS otherwise the basic equipment housing GE of the lithotripter and the monitoring equipment are the same but there may not be a therapeutic head provided. Also, instead of a foot segment to the right hand side of the central segment CS there are two lower leg support troughs US, and a miction through top MB is attached to the left side of the central segment CS, in between the two troughs US. The lithotripter window is in this case closed by the cover AD. The therapeutic head TK is not visible but has simply been pivoted out of the way and is thus not visible so that the area directly in front of the central segment ZS is without restriction and restraint and therefor easily accessible to operating personnel, doctor etc.

FIG. 2 shows, as a separate piece of equipment, an X-ray machine with a curved holder RCB mounted pivotally on the superstructure of a three wheel carriage which can be wheeled around and shifted into the necessary position so that the X-ray head on top is positioned above and the film holder or the like is positioned below. As a patient lies on the rest PR, this equipment reaches around him from above and below. For reasons of this versatility it is desired to make the various parts of the rest transparent to X-ray as much as possible although for the lithotripting version this may not be necessary, if X-rays are not used. X-rays are used sometimes for locating in lithotripter applications and therefore for reasons of versatility indeed the permeability should be very high.

The invention is not limited to the embodiments described above but all changes and modifications thereof, not constituting departures from the spirit and scope of the invention, are intended to be included.

We claim:

1. A lithotripter having a central housing for equipment pertaining to shockwave generation, further having a focusing equipment head movably connected thereto, the improvement comprising
  a patient rest having a central segment extending horizontally from and being mounted to said housing for up and down shifting, the segment being so mounted in cantilever fashion, and having an opening to serve as a treatment window;
  a headrest removably attached to one side of the central segment;
  a leg support structure removably attached to a side of the central segment being opposite to the side of said central segment to which the head rest is attached; and
  said leg support structure being of a two part construction, a first part being similar to said headrest, and a second part being an extension segment, removably attached to a side of the first part that is opposite to a side of said first part where the first part is attached to said central segment.

2. Apparatus as in claim 1, further including an arm removably affixed to said central segment, and at least one lower leg supporting trough being mounted on said arm.

3. Apparatus as in claim 1, including cover means for closing said window.

4. Apparatus as in claim 3, the cover being permeable to X-rays.

5. A lithotripter as in claim 1 including cover means for reducing the dimensions of said window.

* * * * *